United States Patent
Kollipara et al.

(10) Patent No.: US 9,163,261 B2
(45) Date of Patent: Oct. 20, 2015

(54) ADENO-ASSOCIATED VIRUS 2/8—MICRO RNA-101 THERAPY FOR LIVER CANCER

(76) Inventors: Koteswara Rao Kollipara, Hyderabad (IN); Ramesh Babu Batchu, Royal Oak, MI (US)

( * ) Notice: Subject to any disclaimer, the term of this patent is extended or adjusted under 35 U.S.C. 154(b) by 0 days.

(21) Appl. No.: 13/580,552

(22) PCT Filed: Feb. 22, 2011

(86) PCT No.: PCT/IN2011/000104
§ 371 (c)(1),
(2), (4) Date: Aug. 22, 2012

(87) PCT Pub. No.: WO2011/101869
PCT Pub. Date: Aug. 25, 2011

(65) Prior Publication Data
US 2013/0267582 A1    Oct. 10, 2013

(30) Foreign Application Priority Data
Feb. 22, 2010  (IN) .............................. 442/CHE/2010

(51) Int. Cl.
*C07H 21/04* (2006.01)
*C12N 15/861* (2006.01)
*A61K 31/7088* (2006.01)
*C12N 15/86* (2006.01)
*C12N 15/11* (2006.01)

(52) U.S. Cl.
CPC ........ *C12N 15/8613* (2013.01); *A61K 31/7088* (2013.01); *C12N 15/111* (2013.01); *C12N 15/86* (2013.01); *C12N 2310/141* (2013.01); *C12N 2330/51* (2013.01); *C12N 2750/14143* (2013.01); *C12N 2810/6027* (2013.01)

(58) Field of Classification Search
None
See application file for complete search history.

(56) References Cited

PUBLICATIONS

Smits et al. Oncotarget Dec. 2010, 710-720.*

\* cited by examiner

*Primary Examiner* — Kimberly Chong
(74) *Attorney, Agent, or Firm* — Ladas & Parry LLP

(57) ABSTRACT

Adeno-associated virus 2/8-microRNA-101(AAV2/8-miR-101) therapy for liver cancer is provided. In particular, the invention provides a recombinant AAV 2/8 vector, comprising mutated capsid, for the enforced expression of pre-miR-101 and for the treatment of liver cancer.

11 Claims, 7 Drawing Sheets

FIG.1B-1

```
   1 CCTGCAGGCA GCTGCGCGCT CGCTCGCTCA CTGAGGCCGC CCGGGCAAAG
  51 CCCGGGCGTC GGGCGACCTT TGGTCGCCCG GCCTCAGTGA GCGAGCGAGC
 101 GCGCAGAGAG GGAGTGGACT GTGGGAACAT CACAGATTTT GGCTCCATGC
 151 CCTAAAGAGA AATTGGCTTT CAGATTATTT GGATTAAAAA CAAAGACTTT
 201 CTTAACGCGG CCGCTCGGTC CGCACTCGAC CAATTCTCAT GTTTGACAGC
 251 TTATCATCGC AGATCCGGGC AACGTTGTTG CCATTGCTGC AGGCGCAGAA
 301 CTGGTAGGTA TGGAAGATCT ATACATTGAA TCAATATTGG CAATTAGCCA
 351 TATTAGTCAT TGGTTATATA GCATAAATCA ATATTGGCTA TTGGCCATTG
 401 CATACGTTGT ATCTATATCA TAATATGTAC ATTTATATTG GCTCATGTCC
 451 AATATGACCG CCATGTTGAC ATTGATTATT GACTAGTTAT TAATAGTAAT
 501 CAATTACGGG GTCATTAGTT CATAGCCCAT ATATGGAGTT CCGCGTTACA
 551 TAACTTACGG TAAATGGCCC GCCTGGCTGA CCGCCCAACG ACCCCCGCCC
 601 ATTGACGTCA ATAATGACGT ATGTTCCCAT AGTAACGCCA ATAGGGACTT
 651 TCCATTGACG TCAATGGGTG GAGTATTTAC GGTAAACTGC CCACTTGGCA
 701 GTACATCAAG TGTATCATAT GCCAAGTCCG CCCCCTATTG ACGTCAATGA
 751 CGGTAAATGG CCCGCCTGGC ATTATGCCCA GTACATGACC TTACGGGACT
 801 TTCCTACTTG GCAGTACATC TACGTATTAG TCATCGCTAT TACCATGGTG
 851 ATGCGGTTTT GGCAGTACAC CAATGGGCGT GGATAGCGGT TTGACTCACG
 901 GGGATTTCCA AGTCTCCACC CCATTGACGT CAATGGGAGT TTGTTTTGGC
 951 ACCAAAATCA ACGGGACTTT CCAAAATGTC GTAATAACCC CGCCCCGTTG
1001 ACGCAAATGG GCGGTAGGCG TGTACGGTGG GAGGTCTATA TAAGCAGAGC
1051 TCGTTTAGTG AACCGTCAGA TCTCTAGAAG CTGGAACGGC CAGAGAGGCC
1101 TTAAATTCAC CATGGTGAGC AAGCAGATCC TGAAGAACAC CGGCCTGCAG
1151 GAGATCATGA GCTTCAAGGT GAACCTGGAG GGCGTGGTGA ACAACCACGT
1201 GTTCACCATG GAGGGCTGCG GCAAGGGCAA CATCCTGTTC GGCAACCAGC
1251 TGGTGCAGAT CCGCGTGACC AAGGGCGCCC CCCTGCCCTT CGCCTTCGAC
1301 ATCCTGAGCC CCGCCTTCCA GTACGGCAAC CGCACCTTCA CCAAGTACCC
1351 CGAGGACATC AGCGACTTCT TCATCCAGAG CTTCCCCGCC GGCTTCGTGT
1401 ACGAGCGCAC CCTGCGCTAC GAGGACGGCG GCCTGGTGGA GATCCGCAGC
1451 GACATCAACC TGATCGAGGA GATGTTCGTG TACCGCGTGG AGTACAAGGG
1501 CCGCAACTTC CCCAACGACG GCCCCGTGAT GAAGAAGACC ATCACCGGCC
1551 TGCAGCCCAG CTTCGAGGTG GTGTACATGA ACGACGGCGT GCTGGTGGGC
1601 CAGGTGATCC TGGTGTACCG CCTGAACAGC GGCAAGTTCT ACAGCTGCCA
1651 CATGCGCACC CTGATGAAGA GCAAGGGCGT GGTGAAGGAC TTCCCCGAGT
1701 ACCACTTCAT CCAGCACCGC CTGGAGAAGA CCTACGTGGA GGACGGCGGC
1751 TTCGTGGAGC AGCACGAGAC CGCCATCGCC CAGCTGACCA GCCTGGGCAA
1801 GCCCCTGGGC AGCCTGCACG AGTGGGTGTA ATAGCTCGAG AGATCTAAGG
1851 CCTCTCTGGC CTCGACCTCG AGTCTAGCGG CCGCTCGAGG CCGGCAAGGC
1901 CGGATCCAGA CATGATAAGA TACATTGATG AGTTTGGACA AACCACAACT
1951 AGAATGCAGT GAAAAAAATG CTTTATTTGT GAAATTTGTG ATGCTATTGC
2001 TTTATTTGTA ACCATTATAA GCTGCAATAA ACAAGTTAAC AACAACAATT
2051 GCATTCATTT TATGTTTCAG GTTCAGGGGG AGGTGTGGGA GGTTTTTTAA
```

FIG.1B-2

```
2101 AGCAAGTAAA ACCTCTACAA ATGTGGGTCG ACGGTACCAA GCTTGATATC
2151 GAATTCATTA TGCCCAGTAC ATGACCTTAT GGGACTTTCC TACTTGGCAG
2201 TACATCTACG TATTAGTCAT CGCTATTACC ATGGTGATGC GGTTTTGGCA
2251 GTACATCAAT GGGCGTGGAT AGCGGTTTGA CTCACGGGGA TTTCCAAGTC
2301 TCCACCCCAT TGACGTCAAT GGGAGTTTGT TTTGGCACCA AAATCAACGG
2351 GACTTTCCAA AATGTCGTAA CAACTCCGCC CCATTGACGC AAATGGGCGG
2401 TAGGCGTGTA CGGTGGGAGG TCTATATAAG CAGAGCTCGT TTAGTGAACC
2451 GTCAGATCGC CTGGAGACGC CATCCACGCT GTTTTGACCT CCATAGAAGA
          NheI
2501 TTCTAGAGCT AGCGAATTCT ATAAGCAGAG CTCGTTTAGT GAACCGTCAG
2551 ATCGCCTGGA GACGCCATCC ACGCTGTTTT GACCTCCATA GAAGATTCTA
          NheI
2601 GAGCTAGCGC CCTTAATCAT GCAGTTGTTC ATCCTCATTA ATATGGATAA
2651 GTCATGTGTT CATCTTTCAT TCTAATTTAA TTCAACTGGG CCTTTTAATA
2701 TTTCAGCCTC ACCACTTGAT GGGCTCTGAT CCTTCTTTTT CTTCTGCCTC
2751 CTCACGTCTC CAACCAGAAG GTGATCTTTT AGTCCTTCAC TTCATGGGGA
2801 GCCTTCAGAG AGAGTAATGC AGCCACCAGA AAGGATGCCG TTGACCGACA
2851 CAGTGACTGA CAGGCTGCCC TGGCTCAGTT ATCACAGTGC TGATGCTGTC
2901 TATTCTAAAG GTACAGTACT GTGATAACTG AAGGATGGCA GCCATCTTAC
2951 CTTCCATCAG AGGAGCCTCA CCGTACCCAG GAAGAAAGAA GGTGAAAGAG
3001 GAATGTGAAA CAGGTGGCTG GGACCCAGAA ACCCTCTTAC CCTGCACCTC
3051 TGTCATACTT CTCCCGGGGC ATAGGGAGAG TTATTTTGCT TCTCTTTGCC
3101 TTGTTTTGTA ACATGGGCGG CCGGGAAGGA TCTGCGATCG CTCCGGTGCC
                                                  PspOMI
3151 CGTCAGTGGG CAGAGCGCNA CGNNTGNCNN ANNNNNNNNN NNNNGGGCCC
3201 ACGCGTGCGG CCGCAGGAAC CCCTAGTGAT GGAGTTGGCC ACTCCCTCTC
3251 TGCGCGCTCG CTCGCTCACT GAGGCCGGGC GACCAAAGGT CGCCCGACGC
3301 CCGGGCTTTG CCCGGGCGGC CTCAGTGAGC GAGCGAGCGC GCAGCTGCCT
3351 GCAGGACATG TGAGCAAAAG GCCAGCAAAA GGCCAGGAAC CGTAAAAAGG
3401 CCGCGTTGCT GGCGTTTTTC CATAGGCTCC GCCCCCCTGA CGAGCATCAC
3451 AAAAATCGAC GCTCAAGTCA GAGGTGGCGA AACCCGACAG GACTATAAAG
3501 ATACCAGGCG TTTCCCCCTG GAAGCTCCCT CGTGCGCTCT CCTGTTCCGA
3551 CCCTGCCGCT TACCGGATAC CTGTCCGCCT TTCTCCCTTC GGGAAGCGTG
3601 GCGCTTTCTC ATAGCTCACG CTGTAGGTAT CTCAGTTCGG TGTAGGTCGT
3651 TCGCTCCAAG CTGGGCTGTG TGCACGAACC CCCCGTTCAG CCCGACCGCT
3701 GCGCCTTATC CGGTAACTAT CGTCTTGAGT CCAACCCGGT AAGACACGAC
3751 TTATCGCCAC TGGCAGCAGC CACTGGTAAC AGGATTAGCA GAGCGAGGTA
3801 TGTAGGCGGT GCTACAGAGT TCTTGAAGTG GTGGCCTAAC TACGGCTACA
3851 CTAGAAGGAC AGTATTTGGT ATCTGCGCTC TGCTGAAGCC AGTTACCTTC
3901 GGAAAAAGAG TTGGTAGCTC TTGATCCGGC AAACAAACCA CCGCTGGTAG
3951 CGGTGGTTTT TTTGTTTGCA AGCAGCAGAT TACGCGCAGA AAAAAGGAT
4001 CTCAAGAAGA TCCTTTGATC TTTTCTACGG GGTCTGACGC TCAGTGGAAC
```

FIG.1B-3

```
4051 GAAAACTCAC GTTAAGGGAT TTTGGTCATG AGATTATCAA AAAGGATCTT
4101 CACCTAGATC CTTTTAAATT AAAAATGAAG TTTTAAATCA ATCTAAAGTA
4151 TATATGAGTA AACTTGGTCT GACAGTTACC AATGCTTAAT CAGTGAGGCA
4201 CCTATCTCAG CGATCTGTCT ATTTCGTTCA TCCATAGTTG CCTGACTCCC
4251 CGTCGTGTAG ATAACTACGA TACGGGAGGG CTTACCATCT GGCCCCAGTG
4301 CTGCAATGAT ACCGCGAGAC CCACGCTCAC CGGCTCCAGA TTTATCAGCA
4351 ATAAACCAGC CAGCCGGAAG GGCCGAGCGC AGAAGTGGTC CTGCAACTTT
4401 ATCCGCCTCC ATCCAGTCTA TTAATTGTTG CCGGGAAGCT AGAGTAAGTA
4451 GTTCGCCAGT TAATAGTTTG CGCAACGTTG TTGCCATTGC TACAGGCATC
4501 GTGGTGTCAC GCTCGTCGTT TGGTATGGCT TCATTCAGCT CCGGTTCCCA
4551 ACGATCAAGG CGAGTTACAT GATCCCCCAT GTTGTGCAAA AAAGCGGTTA
4601 GCTCCTTCGG TCCTCCGATC GTTGTCAGAA GTAAGTTGGC CGCAGTGTTA
4651 TCACTCATGG TTATGGCAGC ACTGCATAAT TCTCTTACTG TCATGCCATC
4701 CGTAAGATGC TTTTCTGTGA CTGGTGAGTA CTCAACCAAG TCATTCTGAG
4751 AATAGTGTAT GCGGCGACCG AGTTGCTCTT GCCCGGCGTC AATACGGGAT
4801 AATACCGCGC CACATAGCAG AACTTTAAAA GTGCTCATCA TTGGAAAACG
4851 TTCTTCGGGG CGAAAACTCT CAAGGATCTT ACCGCTGTTG AGATCCAGTT
4901 CGATGTAACC CACTCGTGCA CCCAACTGAT CTTCAGCATC TTTTACTTTC
4951 ACCAGCGTTT CTGGGTGAGC AAAAACAGGA AGGCAAATG CCGCAAAAAA
5001 GGGAATAAGG GCGACACGGA AATGTTGAAT ACTCATACTC TTCCTTTTTC
5051 AATATTATTG AAGCATTTAT CAGGGTTATT GTCTCATGAG CGGATACATA
5101 TTTGAATGTA TTTAGAAAAA TAAACAAATA GGGGTTCCGC GCACATTTCC
5151 CCGAAAAGTG CCACCTGACG TCTAAGAAAC CATTATTATC ATGACATTAA
5201 CCTATAAAAA TAGGCGTATC ACGAGGCCCT TTCGTCTCGC GCGTTTCGGT
5251 GATGACGGTG AAAACCTCTG ACACATGCAG CTCCCGGAGA CGGTCACAGC
5301 TTGTCTGTAA GCGGATGCCG GGAGCAGACA AGCCCGTCAG GGCGCGTCAG
5351 CGGGTGTTGG CGGGTGTCGG GGCTGGCTTA ACTATGCGGC ATCAGAGCAG
5401 ATTGTACTGA GAGTGCACCA TAAAATTGTA AACGTTAATA TTTTGTTAAA
5451 ATTCGCGTTA AATTTTTGTT AAATCAGCTC ATTTTTTAAC CAATAGGCCG
5501 AAATCGGCAA AATCCCTTAT AAATCAAAAG AATAGCCCGA GATAGGGTTG
5551 AGTGTTGTTC CAGTTTGGAA CAAGAGTCCA CTATTAAAGA ACGTGGACTC
5601 CAACGTCAAA GGGCGAAAAA CCGTCTATCA GGGCGATGGC CCACTACGTG
5651 AACCATCACC CAAATCAAGT TTTTTGGGGT CGAGGTGCCG TAAAGCACTA
5701 AATCGGAACC CTAAAGGGAG CCCCCGATTT AGAGCTTGAC GGGGAAAGCC
5751 GGCGAACGTG GCGAGAAAGG AAGGGAAGAA AGCGAAAGGA GCGGGCGCTA
5801 GGGCGCTGGC AAGTGTAGCG GTCACGCTGC GCGTAACCAC CACACCCGCC
5851 GCGCTTAATG CGCCGCTACA GGGCGCGTAC TATGGTTGCT TTGACGTATG
5901 CGGTGTGAAA TACCGCACAG ATGCGTAAGG AGAAAATACC GCATCAGGCC
5951 GTAACCTGTC GGATCACCGG AAAGGACCCG TAAAGTGATA ATGATTATCA
6001 TCTACATATC ACAACGTGCG TGGAGGCCAT CAAACCACAA TTCAGGACAG
6051 ACAGTGGCTA CGGCTCAGTT TGGGTTGTGC TGTTGCTGGG CGGCGATGAC
6101 GCCTGTACGC ATTTGGTGAT CCGGTTCTGC TTCCGGTATT CGCTTAATTC
```

FIG.1B-4

```
6151 AGCACAACGG AAAGAGCACT GGCTAACCAG GCTCGCCGAC TCTTCACGAT
6201 TATCGACTCA ATGCTCTTAC CTGTTGTGCA GATATAAAAA ATCCCGAAAC
6251 CGTTATGCAG GCTCTAACTA TTACCTGCGA ACTGTTTCGG GATTGCATTT
6301 TGCAGACCTC TCTGCCTGCG ATGGTTGGAG TTCCAGACGA TACGTCGAAG
6351 TGACCAACTA GGCGGAATCG GTAGTAAGCG CCGCCTCTTT TCATCTCACT
6401 ACCACAACGA GCGAATTAAC CCATCGTTGA GTCAAATTTA CCCAATTTTA
6451 TTCAATAAGT CAATATCATG CCGTTAATAT GTTGCCATCC GTGGCAATCA
6501 TGCTGCTAAC GTGTGACCGC ATTCAAAATG TTGTCTGCGA TTGACTCTTC
6551 TTTGTGGCAT TGCACCACCA GAGCGTCATA CAGCGGCTTA ACAGTGCGTG
6601 ACCAGGTGGG TTGGGTAAGG TTTGGGATTA GCATCGTCAC AGCGCGATAT
6651 GCTGCGCTTG CTGGCATCCT TGAATAGCCG ACGCCTTTGC ATCTTCCGCA
6701 CTCTTTCTCG ACAACTCTCC CCCACAGCTC TGTTTTGGCA ATATCAACCG
6751 CACGGCCTGT ACCATGGCAA TCTCTGCATC TTGCCCCCGG CGTCGCGGCA
6801 CTACGGCAAT AATCCGCATA AGCGAATGTT GCGAGCACTT GCAGTACCTT
6851 TGCCTTAGTA TTTCCTTCAA GCTGCC
```

ADENO-ASSOCIATED VIRUS 2/8—MICRO RNA-101 THERAPY FOR LIVER CANCER

TECHNICAL FIELD OF THE INVENTION

The present invention generally relates to the field of interference RNA (RNAi) and more particularly to a sub-group, micro RNA (miRNA).

BACKGROUND OF INVENTION

Although identified relatively recently, miRNAs have been recognized as one of the major regulatory gene families that utilize identical cellular enzymes/pathways as siRNA with similar mechanisms leading to translational repression of target mRNA. Emerging evidences strongly suggest a crucial role played by miRNAs in various cellular mechanisms including cancer pathogenesis. Micro-RNA genes are transcribed, generally by RNA polymerase II (Pol II), generating the primary miRNA (pri-miRNA). In the nucleus, the RNase III endonuclease Drosha cleaves the pri-miRNA to produce ~70-nucleotide precursor miRNA (pre-miRNA). Exportin-5 transports the pre-miRNA into the cytoplasm, where it is cleaved by another RNase III endonuclease, Dicer, to a ~21-nucleotide miRNA duplex. These miRNA molecules are loaded into RNA-induced silencing complex (RISC) which will help knockdown target messenger RNA.

In the recent past, a particularly important role for miRNAs in cancer pathogenesis has emerged. Virtually all examined tumors globally displayed abnormal miRNA expression contributing to cellular transformation and tumorigenesis. Due to their importance in controlling various cellular functions related to cell division and differences and their dramatic alterations in cancer, potential therapeutic approaches have been envisaged. Several lines of evidences suggest that miRNA replacement represents a viable and efficacious strategy. Although specific miRNAs are often over-expressed in cancer cells, most miRNAs are down regulated in tumors.

Silencing of an abnormally elevated miRNA or enforced expression of under expressed miRNA in cancer are ideal targets for gene correction therapy. Small interfering RNAs and miRNAs share similar endogenous biological processing pathways. miRNA expression and processing can be regulated through similar mechanism that controls siRNA. The similarities between miRNA and siRNA suggest that miRNAs also have the potential to affect epigenetic mechanisms including methylation and histone deacetylation leading to diseases like cancers caused by somatic gene aberrations.

Global miRNA profile studies revealed several specific miRNAs with altered expressions contributing to hepatocyte transformation and metastasis. The role of miRNAs in human cancer is further supported by the fact that >50% of miRNA genes are located at fragile genomic loci prone to deletion or amplification that are frequently altered in human cancers. Correcting the altered micro-RNA genes in liver cancer may constitute an important therapeutic approach. Significant under expression of miRNA-101, is a molecular lesion associated with tumor progression. Genomic loss of miRNA-101 in cancer leads to over expression of EzH2 and concomitant dysregulation of epigenetic pathways, resulting in cancer progression.

miRNAs' have a broad specificity as they do not require a perfect match with the complementary sequence of their target mRNA. This creates a possibility of unintended, non-specific targeting of genes. But the fact that the miR-101 silences the expression of several tumor promoting genes such as COX-2, PKCa, suggests that its enforced expression in cancer cells will knockdown tumor promoting genes. Even though the role of miR1O1 has been studied in several solid epithelial malignancies, relatively little is known about its involvement in the progression of liver cancer.

Enhancer of zeste homolog 2 (EzH2) is a mammalian histone methyltransferase that contributes to the epigenetic silencing of target genes and regulates the survival and metastasis of cancer cells. Of the 34 miRNAs predicted to regulate EzH2, only miR-101 is found to have a strong negative association with cancer progression from benign to localized disease to metastasis. Analysis of human prostate tumors revealed that miR-101 expression decreases during cancer progression, paralleling an increase in EzH2 expression. Expression and function of EzH2 in cancer cell lines are inhibited by microRNA-101 (miR-101).

EzH2 is over expressed in aggressive solid tumors by mechanisms that remain unclear. EzH2 is a catalytic sub-unit of polycomb group of repressor proteins which catalyze methylation of chromatin leading to transcriptional silencing of several tumor suppressor genes or anti-oncogenes. The loss of miR-101 and concomitant elevation of EzH2 is most pronounced in metastatic cancer, suggesting that the loss of miR-101 may represent a progressive molecular lesion in the development of more aggressive disease. Approaches to reintroduce miR-101 into tumors may have therapeutic benefit by reverting the epigenetic program of tumor cells to a more normal state.

Hepato-cellular cancer (HCC) is commonest primary liver cancer accounting for roughly 90% of this class of malignancy with poor prognosis due to rapid spread. Inadequacy of current therapies and presentation of patients with advanced diseases have meant that the treatment is generally palliative and prognosis is extremely grave. Early detection combined with novel effective combinatorial therapies are needed for improving management of HCC patients. The increasing evidences have indicated that miR-101 was regarded as a metastatic determinant and a key component in tumor metastasis in several malignancies including liver cancer.

One of the most difficult challenges impeding the advancement of RNA/-based HCC therapy is efficient and safe delivery of effecter sequences. Ideally, vectors deliver silencing molecules selectively to most if not all the malignant hepatocytes. Viral vectors are generally more efficient vehicles in vivo than non viral vectors. Viral vectors have been successfully used for enforced expression of miRNAs in various gene therapy studies established their delivery and efficacy.

Although viral vectors permit the efficient delivery and stable expression of miRNA, establishment of safety, efficacy and potent gene silencing are crucial ingredients for selecting the viral delivery vehicle. A key area of research in the use of RNA/for clinical applications is the development of a safe delivery method, which to date has involved mainly viral vector systems similar to those suggested for gene therapy.

Adeno-associated virus (AAV) is one of most promising vectors for gene therapy. The recombinant AAV (rAAV) provides a nonpathogenic and latent infection by integrating into the host genome; it also shows high transduction efficiency of both dividing and non-dividing cells and tissues with persistent transgene expression. Such recombinant AAV's have the advantage of exhibiting modified tropism, (i.e., being highly selective with respect to the tissues it infects), as well as having a higher rate of transduction efficiency when compared to native AAV. Adeno-associated virus (AAV) is currently being tested in several human gene therapy trials because of its several unique features that distinguish it from other gene therapy vectors. These features include (i) a broad host range; (ii) lack of cell-mediated immune response against the vector; (iii) ability to integrate into a host chromosome or persist episomally, thereby creating potential for long-term expression; (iv) minimal influence on changing the pattern of cellular gene expression and the like.

Hence there is a need for a treatment for liver cancer incorporating the expression of pre-miR-101.

OBJECT OF INVENTION

The principal object of the invention is to provide a treatment of liver cancer by utilizing a vector for enforced expression of pre-miR-101.

STATEMENT OF INVENTION

Accordingly the invention provides a vector for enforced expression of pre-miR-101 which is characterized by a vector of polynucleotide sequence of SEQ ID NO:1.

There is also provided a pharmaceutical composition for enforced expression of pre-miR-101 which is characterized by a vector of polynucleotide sequence of SEQ ID NO: 1 and a pharmaceutically acceptable carrier.

In another embodiment, the invention provides a method for enforced expression of pre-miR-101 by administering a vector of polynucleotide sequence of SEQ ID NO: 1.

In yet another embodiment, the invention provides a method for treating a patient having a disease associated with over expression of EzH2 by administering to the patient a therapeutically effective amount of a vector of polynucleotide sequence of SEQ ID NO:1.

BRIEF DESCRIPTION OF FIGURES

The embodiments are better illustrated in the accompanying drawings, through out which reference letters indicate corresponding parts in the various figures. The embodiments herein will be better understood from the following description with reference to the drawings, in which:

FIGS. 1B-1, 1B-2, 1B-3 and 1B-4 are schematic diagrams depicting a consensus nucleotide sequence of chimeric virus vector, AAV-8-pre-miRNA-101 and is represented by SEQ ID NO:1.

FIG. 3 A is a schematic diagram depicting subcutaneous tumor growth in SCID mice injected with control Hep-G2 cells.

DETAILED DESCRIPTION OF INVENTION

Figure 1A:
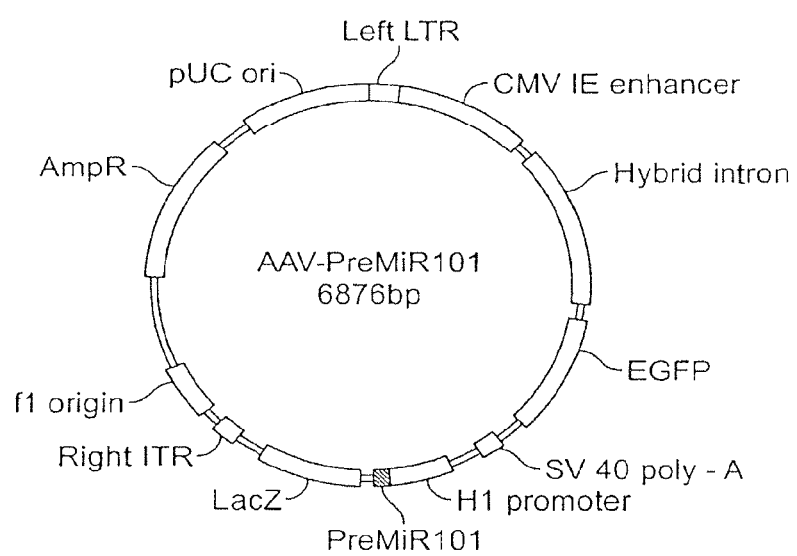
FIG. 1A is a Schematic diagram depicting the construction of recombinant vector, AAV-8-pre-miRNA-1O1, a cloned pre-miRNA-101 ORF in a rAAV-8.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

It is to be understood that the present disclosure is not limited in its application to the details of construction and the arrangement of components set forth in the following description or illustrated in the drawings. The present disclosure is capable of other embodiments and of being practiced or of being carried out in various ways. Also, it is to be understood that the phraseology and terminology used herein is for the purpose of description and should not be regarded as limiting.

The use of "including", "comprising" or "having" and variations thereof herein is meant to encompass the items listed thereafter and equivalents thereof as well as additional items. The terms "a" and "an" herein do not denote a limitation of quantity, but rather denote the presence of at least one of the referenced item. Further, the use of terms "first", "second", and "third", and the like, herein do not denote any order, quantity, or importance, but rather are used to distinguish one element from another.

One embodiment is directed towards the construction and expression of a chimeric virus vector, AAV-2-pre-miRNA-101, wherein an entire pre-miRNA-101 ORF is cloned in a recombinant adeno-associated virus vector serotype-2, pseudo-typed with AAV-8 capsids; wherein the capsids are mutated from tyrosine to phenylalanine at 3 different places (Y: Tyrosine; F: Phenylalanine; Y444F, Y500F and Y730F) Subsequently expressed miRNA-101 molecules target EzH2 among other metastsasis associated transcripts in HCC. The vector based medicine in a pharmaceutically acceptable carrier, wherein the pharmaceutically acceptable carrier includes without limitation simple saline and buffer, is either directly administered through hepatic portal vein or intravenous injection of subjects that achieves tumor regression.

The embodiments are better illustrated in the accompanying drawings, throughout which like reference letters indicate corresponding parts in the various figures: Referring now to the drawings, and more particularly to FIG. 1A, FIG. 1B-1, 1B-2, 1B-3, 1B-4, FIG. 2A, FIG. 2B, FIG. 2C, FIG. 3A, FIG. 3B, where there are shown preferred embodiments.

Referring to FIG. 1A is a diagram depicting the construction of AAV-2-pre-miRNA-101, a recombinant virus vector where an entire pre-miRNA-101 ORF is cloned into multiple cloning site of AAV-2 vector. In accordance with an embodiment, the vector constructed is a self-complementary AAV vector in which the expression of pre-miRNA-101 is being driven by human HI promoter. According to an embodiment the self-complementary adeno-associated virus (scAAV) vector contains mutated capsids, wherein mutation(s) result in an amino acid substitution of the capsid protein at critical amino acid positions. Adeno-associated viruses, from the parvovirus family, are small viruses with a genome of single stranded DNA. The recombinant AAV, which does not contain any viral genes and only the therapeutic gene, does not integrate into the genome. Instead the recombinant viral genome fuses at its ends via inverted terminal repeat (ITR) recombination to form circular, episomal forms which contributes to the long term gene expression. The vector also accommodates many functional genes of variable functions and several marker genes to help the functional analysis of a gene of interest. Recombinant AAV vectors containing the miRNA expression cassette can be packaged efficiently and can be used to infect successfully the target cells at high frequency and with minimal toxicity. Assembly of viral vector can be done using processes well known in the art.

Referring to FIGS. 1B-1, 1B-2, 1B-3 and 1B-4 are schematic diagrams depicting the consensus nucleotide sequence of a chimeric, self-complementary AAV-2-pre-miRNA-101 and represents SEQ ID NO:1. In accordance with an embodiment, vector comprises the restriction endonuclease sites, Nhel, PspOMI and the like. A self-complementary adeno-associated virus (scAAV) vector also known as double-stranded AAV (dsAAV) is employed which significantly minimizes the vector load required to achieve sustained transgene expression. The efficiency of these vectors in terms of the number of genome-containing particles required for transduction is hindered by the need to convert the single-stranded DNA (ssDNA) genome into double-stranded DNA (dsDNA) prior to expression. This step can be entirely circumvented through the use of self-complementary vectors, which package an inverted repeat genome that can fold into dsDNA without the requirement for DNA synthesis or base-pairing between multiple vector genomes.

Figure 2A:
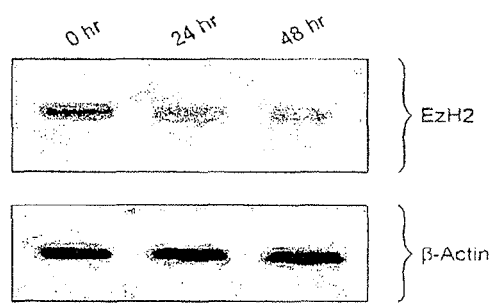
FIG. 2A is a schematic diagram depicting a Western blot showing the expression of AAV-miRNA-101 effected EzH2 after 24 and 48 hrs using beta-actin as loading control.

Referring to FIG. 2A is a diagram depicting a Western blot showing the expression of AAV-miRNA-101 effected EzH2 after 24 and 48 hrs using beta-actin as loading control. According to an embodiment, these cancer cells are cultured for indicated time intervals after AAV-miRNA-101 transduction. The Western blot analysis illustrates a diminished EzH2 expression through scanty bands on the blotting gel. Persistent miRNA-101 expression is highly desirable to inhibit EzH2,
which requires an uninterrupted expression of miRNA-101 from precursor miRNA (pre-miRNA). This is possible if a pre-miRNA-101 is transduced into cells as part of a plasmid or introduced by recombinant viral vectors. This pre-miRNA generates a single stem-loop of sense and antisense strands that are cleaved by the Dicer to produce the active miRNA. miRNA-101 silences the EzH2 transcript and protein expression of polycomb repression complex protein through binding to the 3'UTR of EzH2 transcript, thus resulting in the down-regulation of the EzH2 transcript. microRNAs (miRNAs) regulate target gene expression through translation repression or mRNA degradation. The ability of individual miRNAs to regulate hundreds of transcripts allows these RNAs to coordinate complex programs of gene expression and thereby induce global changes in cellular physiology. miRNAs provide functions essential for normal development and cellular homeostasis and accordingly dysfunction of these molecules has been linked to several human diseases. RNA interference (RNA/) is a mechanism by which double stranded RNAs mediate sequence-specific gene silencing. This provides a new tool in the fight against cancer. The application of RNA/technology in basic cancer research facilitates the identification and validation of potential therapeutic targets for cancer, and the elucidation of the molecular pathways governing cancer growth and development.

Figure 2B:
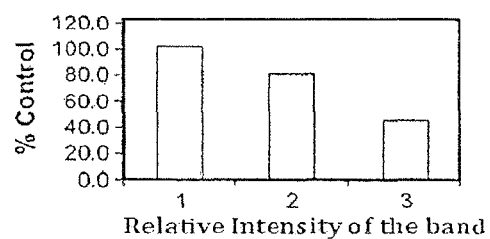
FIG. 2B is a schematic diagram depicting a graphical illustration of the effect of AAV-miRNA-101 on the growth of Hep-G2 cells.

Referring to FIG. 2B is a diagram depicting a graphical illustration of the effect of AAV-miRNA-101 on the growth of Hep-G2 cells. These cancer cells are cultured for indicated time intervals after AAV-miRNA-101 transduction. This diagram illustrates the inhibitory effect of AAV-miRNA-101 vector on EzH2 expression as "% control" according to one embodiment. AAV-miRNA can initiate long-term transgene expression and this transduction is attributed to episomal concatamer formation without integration into host chromosome. Based on this point, AAV vectors would appear less mutagenic. Although AAV package capacity is restrained to less than 5 kb, most of therapeutic genes for cancer treatment fall into this range. Fast kinetics of gene expression when delivered as scAAV vector is attributed to the conversion of ssAAV vector genome to double-stranded templates. This advancement, which further reduces AAV packaging size (2.5 kb), will still accommodate pre-microRNA which in general is less than 100 nucleotides long.

Figure 2C:
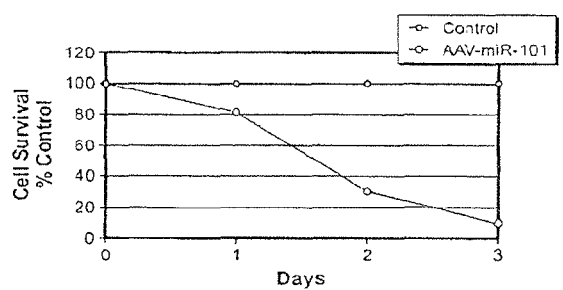
FIG. 2C is a schematic diagram depicting growth curves of Hep-G2 cells transduced by AAV-miR-101.

Referring to FIG. 2C is a diagram depicting the growth curves of Hep-G2 cells transduced by AAV-miR-101 vector. Cell growth is assessed by CCK-8 cell proliferation assay method. According to an embodiment, Hep-52 cancer cell lines are transduced by AAV-miRNA-101 and cultured over a period of 3 days. The transduced cells result in time dependent inhibition of cell proliferation and induced cell death. These diagrams illustrate the time dependent inhibitory effect of AAV-miRNA-101 vector on EzH2 expression according to one embodiment. EzH2 is one of a set of 70 genes whose expression predicts a poor outcome in HCC and most patients with high EzH2 exhibit this poor prognosis signature. EzH2 over expression correlates with late stage disease and can even be an independent predictor of aggressive cancers.

Figure 3A:
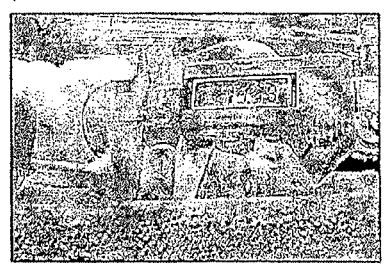
Figure 3B:
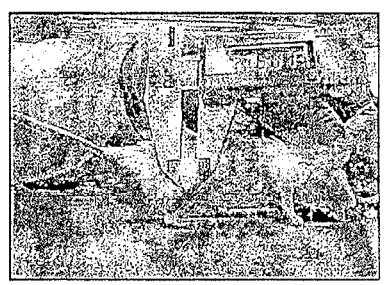
FIG. 3B is a schematic diagram depicting subcutaneous tumor growth in SCID injected with Hep-G2 cells transduced by AAV-miR-101.

Referring to FIG. 3A is a diagram depicting the measurement of tumor found after 8 weeks when ~3 million control Hep-G2 cells were subcutaneously injected in a 6 week old SCID mice. Whereas FIG. 3B is a diagram depicting the measurement of tumor found after 8 weeks when ~3 million AV-miR-101 transduced Hep-G2 cells were subcutaneously injected in 6 week old SCID mice. The tumor-forming ability of Hep-G2 cancer cell lines was found to be substantially reduced when they were transduced by AAV-miRNA-101, clearly indicating that EzH2 is needed for the growth of liver tumors in vivo.

In a preferred embodiment, the AAV vector contains mutation(s) resulting in an amino acid substitution of the capsid protein at critical amino acid positions. According to an embodiment, recombinant AAV vectors which show a reduced or eliminated heparin binding function can be achieved by replacing amino acid residues located, at critical positions (Y: Tyrosine; F: Phenylalanine; Y444F, Y500F and Y730F). Alternatively, amino acid residues at critical positions can be eliminated or one or more amino acid residues can be inserted thereby distorting the
spatial structure of the heparin binding domain in such a way that heparin binding is eliminated or at least weakened.

AAV8, a serotype discovered in rhesus monkeys is a remarkable alternative to AAV2 because it is able to mediate robust transgene expression in various tissues, particularly for mouse liver transduction. Use of pseudo typed vectors of the AAV2 type genome, packaged in AAV8 capsids, is characterized by a more rapid rise in transgene expression as well as an unrestricted level of hepatocyte transduction, an ~20 times higher than found with prototype AAV2 vectors. AAV8 vectors facilitates an efficient hepatocyte transduction by means of either a portal vein or tail vein injection equally, which otherwise not practical using prototype AAV2 vectors.

According to an embodiment, targeted gene silencing of liver cancer metastasis associated gene EzH2, by RNA interference (RNAi) mediated by recombinant vector, AAV-miRNA-101 can inhibit liver cancer progression in vitro and in vivo. The miRNA expressed from viral vectors in vitro and in vivo specifically reduce expression of stably expressed plasmids in cells, endogenous genes and transgenes in animal models. The ability of viral vectors based on AAV to transduce cells efficiently in specific tissues, coupled with effectiveness of virally expressed siRNA will extend the application of siRNA to viral-based therapies and to basic research.

As will be appreciated by a person skilled in the art, the embodiments provide a variety of advantages. As per an embodiment, using a pre-miRNA-101 cloned in a self-complementary AAV-2 vector to express miRNA, targets and silences EzH2, which is a metastasis promoting gene in liver cancer apart from other tumor promoting genes. It offers an efficient and safe therapeutic option to arrest the progression of metastasizing hepatocellular carcinoma and other metastasizing cancers in vitro and in vivo. This recombinant vector administered in a pharmaceutically acceptable carrier molecule or formulation can be used as an adjuvant therapy after surgery or in combination with surgical treatment. If given as a direct infusion in to hepatic portal vein or through intra-arterial administration, it can result in a targeted and faster elimination of hepatic cancer cells. As per an embodiment, various cytotoxic side affects associated with many chemotherapeutic agents and specific to cancer cells is evaced without causing severe side effects. As per one embodiment, the drug can be administered directly into hepatic portal vein, which exposes the tumor to very high doses of the drug than systemic infusion. Further intravenous administration of AAV8 is known to target liver tissue. An increased drug exposure achieved by the vector based medicine results in tumor regression more significantly than systemic drug delivery and also eliminates any possible side effects on other organs.

Applying new generation rAAV vectors for gene silencing that are not only self-complimentary AAV-2 vectors (scAAV-2) for efficient trans-gene expression but also have capsid mutations which circumvent cytosomal degradation and enhance the transduction by 20 fold leading to high-efficiency transduction at low doses. miRNAs have favorable pharmacokinetic properties and can be delivered to a wide range of organs. miRNA based therapeutics offer a highly selective gene therapy to several metastatic cancers including liver cancer in subjects who failed to respond to conventional therapies through a specific post transcriptional gene silencing mechanism.

While specific embodiments have been shown and described in detail to illustrate the inventive principles, it will be understood that the invention may be embodied otherwise without departing from such principles.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

We claim:

1. A vector for enforced expression of pre-miR-101 comprising a polynucleotide sequence of SEQ ID NO:1.

2. The vector for enforced expression of pre-miR-101 as claimed in claim 1, wherein the vector is recombinant AAV2/8 vector.

3. The vector for enforced expression of pre-miR-101 as claimed in claim 2, wherein the recombinant AAV2/8 vector comprises of a modified capsid.

4. The vector for enforced expression of pre-miR-101 as claimed in claim 3, wherein the modified capsid comprises of at least one amino acid substitution.

5. The vector for enforced expression of pre-miR-101 as claimed in claim 4, wherein the amino acid substitution comprises of substituting tyrosine with phenylalanine.

6. The vector for enforced expression of pre-miR-101 as claimed in claim 4, wherein the amino acid substitution occurs at least one of Y444F, Y500F and Y730F.

7. A cell line comprising a vector for enforced expression of pre-miR-101, wherein said vector comprises of a polynucleotide sequence of SEQ ID NO: 1.

8. A pharmaceutical composition for enforced expression of pre-miR-101 comprising: a vector of polynucleotide sequence of SEQ ID NO: 1; and a pharmaceutically acceptable carrier.

9. A method for enforced expression of pre-miR-101 comprising: administering to a subject a vector of polynucleotide sequence of SEQ ID NO: 1.

10. A method for treating a patient having a cancer, comprising: administering to a patient a therapeutically effective amount of a vector of polynucleotide sequence of SEQ ID NO: 1.

11. The method as claimed in claim 10, wherein the cancer is hepato-cellular cancer.

* * * * *

SEQUENCE LISTING

```
<160> NUMBER OF SEQ ID NOS: 1

<210> SEQ ID NO 1
<211> LENGTH: 6876
<212> TYPE: DNA
<213> ORGANISM: recombinant adeno-associated virus-2/8
<220> FEATURE:
<221> NAME/KEY: misc_feature
<222> LOCATION: (3169)..(3169)
<223> OTHER INFORMATION: n is a, c, g, or t
<220> FEATURE:
<221> NAME/KEY: misc_feature
<222> LOCATION: (3173)..(3174)
<223> OTHER INFORMATION: n is a, c, g, or t
<220> FEATURE:
<221> NAME/KEY: misc_feature
<222> LOCATION: (3177)..(3177)
<223> OTHER INFORMATION: n is a, c, g, or t
<220> FEATURE:
<221> NAME/KEY: misc_feature
<222> LOCATION: (3179)..(3180)
<223> OTHER INFORMATION: n is a, c, g, or t
<220> FEATURE:
<221> NAME/KEY: misc_feature
<222> LOCATION: (3182)..(3194)
<223> OTHER INFORMATION: n is a, c, g, or t

<400> SEQUENCE: 1
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggact     120
gtgggaacat cacagatttt ggctccatgc cctaaagaga aattggcttt cagattattt     180
ggattaaaaa caaagacttt cttaacgcgg ccgctcggtc cgcactcgac caattctcat     240
gtttgacagc ttatcatcgc agatccgggc aacgttgttg ccattgctgc aggcgcagaa     300
ctggtaggta tggaagatct atacattgaa tcaatattgg caattagcca tattagtcat     360
tggttatata gcataaatca atattggcta ttggccattg catacgttgt atctatatca     420
```

-continued

```
taatatgtac atttatattg gctcatgtcc aatatgaccg ccatgttgac attgattatt    480
gactagttat taatagtaat caattacggg gtcattagtt catagcccat atatggagtt    540
ccgcgttaca taacttacgg taaatggccc gcctggctga ccgcccaacg acccccgccc    600
attgacgtca ataatgacgt atgttcccat agtaacgcca atagggactt tccattgacg    660
tcaatgggtg gagtatttac ggtaaactgc ccacttggca gtacatcaag tgtatcatat    720
gccaagtccg cccctattg acgtcaatga cggtaaatgg cccgcctggc attatgccca    780
gtacatgacc ttacgggact ttcctacttg gcagtacatc tacgtattag tcatcgctat    840
taccatggtg atgcggtttt ggcagtacac caatgggcgt ggatagcggt ttgactcacg    900
gggatttcca agtctccacc ccattgacgt caatgggagt ttgttttggc accaaaatca    960
acgggacttt ccaaaatgtc gtaataaccc cgccccgttg acgcaaatgg gcggtaggcg   1020
tgtacggtgg gaggtctata taagcagagc tcgtttagtg aaccgtcaga tctctagaag   1080
ctggaacggc cagagaggcc ttaaattcac catggtgagc aagcagatcc tgaagaacac   1140
cggcctgcag gagatcatga gcttcaaggt gaacctggag ggcgtggtga acaaccacgt   1200
gttcaccatg gagggctgcg gcaagggcaa catcctgttc ggcaaccagc tggtgcagat   1260
ccgcgtgacc aagggcgccc ccctgccctt cgccttcgac atcctgagcc ccgccttcca   1320
gtacggcaac cgcaccttca ccaagtaccc cgaggacatc agcgacttct tcatccagag   1380
cttccccgcc ggcttcgtgt acgagcgcac cctgcgctac gaggacgcg gcctggtgga   1440
gatccgcagc gacatcaacc tgatcgagga gatgttcgtg taccgcgtgg agtacaaggg   1500
ccgcaacttc cccaacgacg gccccgtgat gaagaagacc atcaccggcc tgcagcccag   1560
cttcgaggtg gtgtacatga cgacggcgt gctggtgggc caggtgatcc tggtgtaccg   1620
cctgaacagc ggcaagttct acagctgcca catgcgcacc ctgatgaaga gcaagggcgt   1680
ggtgaaggac ttccccgagt accacttcat ccagcaccgc ctggagaaga cctacgtgga   1740
ggacggcggc ttcgtggagc agcacgagac cgccatcgcc cagctgacca gcctgggcaa   1800
gcccctgggc agcctgcacg agtgggtgta atagctcgag agatctaagg cctctctggc   1860
ctcgacctcg agtctagcgg ccgctcgagg ccggcaaggc cggatccaga catgataaga   1920
tacattgatg agtttggaca aaccacaact agaatgcagt gaaaaaaatg ctttatttgt   1980
gaaatttgtg atgctattgc tttatttgta accattataa gctgcaataa acaagttaac   2040
aacaacaatt gcattcattt tatgtttcag gttcaggggg aggtgtggga ggttttttaa   2100
agcaagtaaa acctctacaa atgtgggtcg acggtaccaa gcttgatatc gaattcatta   2160
tgcccagtac atgaccttat gggactttcc tacttggcag tacatctacg tattagtcat   2220
cgctattacc atggtgatgc ggttttggca gtacatcaat gggcgtggat agcggtttga   2280
ctcacgggga tttccaagtc tccaccccat tgacgtcaat gggagtttgt tttggcacca   2340
aaatcaacgg gactttccaa aatgtcgtaa caactccgcc ccattgacgc aaatgggcgg   2400
taggcgtgta cggtgggagg tctatataag cagagctcgt ttagtgaacc gtcagatcgc   2460
ctggagacgc catccacgct gttttgacct ccatagaaga ttctagagct agcgaattct   2520
ataagcagag ctcgtttagt gaaccgtgag atcgcctgga cgccatccac gctgttttt   2580
gacctccata gaagattcta gagctagcgc ccttaatcat gcagttgttc atcctcatta   2640
atatggataa gtcatgtgtt catctttcat tctaatttaa ttcaactggg ccttttaata   2700
tttcagcctc accacttgat gggctctgat ccttcttttt cttctgcctc ctcacgtctc   2760
caaccagaag gtgatctttt agtccttcac ttcatgggga gccttcagag agagtaatgc   2820
```

```
agccaccaga aaggatgccg ttgaccgaca cagtgactga caggctgccc tggctcagtt    2880
atcacagtgc tgatgctgtc tattctaaag gtacagtact gtgataactg aaggatggca    2940
gccatcttac cttccatcag aggagcctca ccgtacccag gaagaaagaa ggtgaaagag    3000
gaatgtgaaa caggtggctg ggacccagaa accctcttac cctgcacctc tgtcatactt    3060
ctcccggggc atagggagag ttattttgct tctctttgcc ttgttttgta acatgggcgg    3120
ccgggaagga tctgcgatcg ctccggtgcc cgtcagtggg cagagcgcna cgnntgncnn    3180
annnnnnnnn nnnngggccc acgcgtgcgg ccgcaggaac cctagtgat ggagttggcc     3240 actccctctc tgcgcgctcg ctcgctcact gaggccgggc gaccaaaggt cgcccgacgc    3300
ccgggctttg cccgggcggc ctcagtgagc gagcgagcgc gcagctgcct gcaggacatg    3360
tgagcaaaag gccagcaaaa ggccaggaac cgtaaaaagg ccgcgttgct ggcgtttttc    3420
cataggctcc gcccccctga cgagcatcac aaaaatcgac gctcaagtca gaggtggcga    3480
aacccgacag gactataaag ataccaggcg tttccccctg gaagctccct cgtgcgctct    3540
cctgttccga ccctgccgct taccggatac ctgtccgcct ttctcccttc gggaagcgtg    3600
gcgctttctc atagctcacg ctgtaggtat ctcagttcgg tgtaggtcgt tcgctccaag    3660
ctgggctgtg tgcacgaacc ccccgttcag cccgaccgct gcgccttatc cggtaactat    3720
cgtcttgagt ccaacccggt aagacaggac ttatcgccac tggcagcagc cactggtaac    3780
aggattagca gagcgaggta tgtaggcggt gctacagagt tcttgaagtg gtggcctaac    3840
tacggctaca ctagaaggac agtatttggt atctgcgctc tgctgaagcc agttaccttc    3900
ggaaaaagag ttggtagctc ttgatccggc aaacaaacca ccgctggtag cggtggtttt    3960
tttgtttgca agcagcagat tacgcgcaga aaaaaggat ctcaagaaga tcctttgatc     4020
ttttctacgg ggtctgacgc tcagtggaac gaaaactcac gttaagggat tttggtcatg    4080
agattatcaa aaaggatctt cacctagatc cttttaaatt aaaaatgaag ttttaaatca    4140
atctaaagta tatatgagta aacttggtct gacagttacc aatgcttaat cagtgaggca    4200
cctatctcag cgatctgtct atttcgttca tccatagttg cctgactccc cgtcgtgtag    4260
ataactacga tacgggaggg cttaccatct ggccccagtg ctgcaatgat accgcgagac    4320
ccacgctcac cggctccaga tttatcagca ataaaccagc cagccggaag ggccgagcgc    4380
agaagtggtc ctgcaacttt atccgcctcc atccagtcta ttaattgttg ccgggaagct    4440
agagtaagta gttcgccagt taatagtttg cgcaacgttg ttgccattgc tacaggcatc    4500
gtggtgtcac gctcgtcgtt tggtatggct tcattcagct ccggttccca acgatcaagg    4560
cgagttacat gatcccccat gttgtgcaaa aaagcggtta gctccttcgg tcctccgatc    4620
gttgtcagaa gtaagttggc cgcagtgtta tcactcatgg ttatggcagc actgcataat    4680
tctcttactg tcatgccatc cgtaagatgc ttttctgtga ctggtgagta ctcaaccaag    4740
tcattctgag aatagtgtat gcggcgaccg agttgctctt gcccggcgtc aatacgggat    4800
aataccgcgc cacatagcag aactttaaaa gtgctcatca ttggaaaacg ttcttcgggg    4860
cgaaaactct caaggatctt accgctgttg agatccagtt cgatgtaacc cactcgtgca    4920
cccaactgat cttcagcatc ttttactttc accagcgttt ctgggtgagc aaaaacagga    4980
aggcaaaatg ccgcaaaaaa gggaataagg gcgacacgga aatgttgaat actcatactc    5040
ttcctttttc aatattattg aagcatttat cagggttatt gtctcatgag cggatacata    5100
tttgaatgta tttagaaaaa taaacaaata ggggttccgc gcacatttcc ccgaaaagtg    5160
ccacctgacg tctaagaaac cattattatc atgacattaa cctataaaaa taggcgtatc    5220
```

```
-continued acgaggccct ttcgtctcgc gcgtttcggt gatgacggtg aaaacctctg acacatgcag    5280
ctcccggaga cggtcacagc ttgtctgtaa gcggatgccg ggaggagaca agcccgtcag    5340
ggcgcgtcag cgggtgttgg cgggtgtcgg ggctggctta actatgcggc atcagagcag    5400
attgtactga gagtgcacca taaaattgta aacgttaata ttttgttaaa attcgcgtta    5460 aattttgtt aaatcagctc atttttaac cataggccg aaatcggcaa aatcccttat      5520
aaatcaaaag aatagcccga gatagggttg agtgttgttc cagtttggaa caagagtcca    5580
ctattaaaga acgtggactc caacgtcaaa gggcgaaaaa ccgtctatca gggcgatggc    5640
ccactacgtg aaccatcacc caaatcaagt tttttggggt cgaggtgccg taaagcacta    5700
aatcggaacc ctaaagggag cccccgattt agagcttgac ggggaaagcc ggcgaacgtg    5760
gcgagaaagg aagggaagaa agcgaaagga gcgggcgcta gggcgctggc aagtgtagcg    5820
gtcacgctgc gcgtaaccac cacacccgcc gcgcttaatg cgccgctaca gggcgcgtac    5880
tatggttgct ttgacgtatg cggtgtgaaa taccgcacag atgcgtaagg agaaaatacc    5940
gcatcaggcc gtaacctgtc ggatcaccgg aaaggacccg taaagtgata atgattatca    6000
tctacatatc acaacgtgcg tggaggccat caaaccacaa ttcaggacag acagtggcta    6060
cggctcagtt tgggttgtgc tgttgctggg cggcgatgac gcctgtacgc atttggtgat    6120
ccggttctgc ttccggtatt cgcttaattc agcacaacgg aaagagcact ggctaaccag    6180
gctcgccgac tcttcacgat tatcgactca atgctcttac ctgttgtgca gatataaaaa    6240
atcccgaaac cgttatgcag gctctaacta ttacctgcga actgtttcgg gattgcattt    6300
tgcagacctc tctgcctgcg atggttggag ttccagacga tacgtcgaag tgaccaacta    6360
ggcggaatcg gtagtaagcg ccgcctcttt tcatctcact accacaacga gcgaattaac    6420
ccatcgttga gtcaaattta cccaatttta ttcaataagt caatatcatg ccgttaatat    6480
gttgccatcc gtggcaatca tgctgctaac gtgtgaccgc attcaaaatg ttgtctgcga    6540
ttgactcttc tttgtggcat tgcaccacca gagcgtcata cagcggctta acagtgcgtg    6600
accaggtggg ttgggtaagg tttgggatta gcatcgtcac agcgcgatat gctgcgcttg    6660
ctggcatcct tgaatagccg acgcctttgc atcttccgca ctctttctcg acaactctcc    6720
cccacagctc tgttttggca atatcaaccg cacggcctgt accatggcaa tctctgcatc    6780 ttgccccgg cgtcgcggca ctacggcaat aatccgcata agcgaatgtt gcgagcactt    6840
gcagtacctt tgccttagta tttccttcaa gctgcc                              6876
```